(12) United States Patent
Nie et al.

(10) Patent No.: US 8,402,811 B2
(45) Date of Patent: Mar. 26, 2013

(54) CYCLIC IMPACT-SLIDING FATIGUE WEAR TESTING INSTRUMENT

(76) Inventors: Yining Nie, Windsor (CA); Jingzeng Zhang, Windsor (CA)

(*) Notice: Subject to any disclaimer, the term of this patent is extended or adjusted under 35 U.S.C. 154(b) by 365 days.

(21) Appl. No.: 12/824,172

(22) Filed: Jun. 26, 2010

(65) Prior Publication Data

US 2011/0314894 A1    Dec. 29, 2011

(51) Int. Cl.
*G01M 7/00* (2006.01)
(52) U.S. Cl. .................................................. 73/12.09
(58) Field of Classification Search .................. 73/12.09
See application file for complete search history.

(56) References Cited

FOREIGN PATENT DOCUMENTS

EP         1320681    *   6/1987

* cited by examiner

*Primary Examiner* — Lisa Caputo
*Assistant Examiner* — Octavia Davis-Hollington

(57) ABSTRACT

This invention deals with a testing instrument that is used to investigate failure behavior of items subject to impact and sliding forces. The testing instrument produces an impact motion and a sliding motion in each testing cycle with maximum contact pressure similar to actual stresses applied to the items during real applications. The invented instrument simulates wear conditions and failure behaviors of biomedical implants, components, tools and coatings which are observed in practical applications.

17 Claims, 3 Drawing Sheets

CYCLIC IMPACT-SLIDING FATIGUE WEAR TESTING INSTRUMENT

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

DESCRIPTION

Background of the Invention

Due to the increasing use of advanced materials, tool wear prevention has become an important issue in the manufacturing and machining of those materials. For instance, die wear can be a problem during the stamping of advanced high strength steels (AHSS) for production of automotive parts. New die materials, surface treatment and coatings technology have to be developed to solve wear problems. The die materials include H13, P20, S7, D2, M2 and other tool steels. Surface treatment includes quench hardening, flame hardening, laser hardening, induction hardening, nitriding, carburizing and nitrocarburizing. The surface coatings include electroplated or electroless coatings, plasma and thermal spraying, physical vapor deposition (PVD), and chemical vapor deposition (CVD) coatings. Among the surface engineering technologies described above, PVD and CVD coatings have been considered as necessary top layers on die and tool surfaces to battle wear problems in a wide range of applications.

Because the PVD and CVD coatings are usually a thin ceramic layer deposited on the tool steels and cements (e.g., WC—Co), evaluation of the coating properties becomes very challenging. For the metal forming applications where the combination of impact and sliding forces is applied, there exist different failure behaviors of the hard PVD and CVD coatings. Peeling, chipping, circular cracking and fatigue cracking can be the coating failure mechanisms under ultra-high contact stresses during the metal-forming. However, currently available laboratory tests on the hard coatings use operating conditions that do not correspond to actual stress situations and levels of stamping die production, thus the lab tests cannot replicate the coating failure phenomena. For instance, pin-on-disc tribotests only simulate static sliding forces without an impact load applied. A ball-on-plate impact tester [Surface & Coatings Technology, 75 (1995) pp 857-868] can only perform vertical impacting without a sliding motion. There is no laboratory testing method or instrument that can be effectively used to produce a combination of an impact motion and a sliding motion in each testing cycle with maximum contact pressures similar to actual contact stresses applied to dies, tools and coatings in metal-manufacturing production.

Biomedical implants such as hip and knee replacement with and without PVD/CVD coatings also suffer from impact-sliding wear failures caused by impact and sliding forces.

Thus, this invention deals with a testing instrument that can be cost-effectively used to investigate fatigue cracking and wear failure behaviour of dies, tools, coatings and bioimplants under practical application conditions.

SUMMARY OF THE INVENTION

In this invention, a cyclic impact-sliding fatigue wear tester is developed for accelerated tests to investigate the failure behavior of bioimplants, components, dies and coatings subject to impact fatigue and sliding fatigue wear under very high contact stresses. The test instrument mainly comprises one driving force generation device, one impact body connected to the shaft of the driving force generation device, one rocker with a sample holder on one arm and a rebounding force generation device used to apply pre-loading on the other arm, one rigid frame to hold all the above parts together, one driving force control system, one switch control system, one load cell and one data acquisition system.

The testing instrument produces an impact motion and a sliding motion in each testing cycle. The impact and reciprocating sliding frequency is 1 to 20 Hertz (Hz). The number of cycles is set up at 1,000 to 100,000 cycles. The instrument can produce 0.5-4.5 GigaPascals (GPa) maximum contact pressure during the tests. After a number of testing cycles, the wear conditions and failure behaviors on the sample surfaces and cross sections can be investigated using optical and electron microscopes.

The testing instrument is used for a better understanding of failure behavior of dies, moulds, tools, and coatings so that the strategic use of advanced tool materials and hard coatings will be one of the solutions in dealing with the wear problems that occur in metal-forming, manufacturing, die-casting, and biomedical implants. Recommendations on coating and tool substrate materials selections, methods for substrate surface preparation, and coating deposition processes can be made after the better understanding of failure mechanisms.

DETAILED DESCRIPTION OF THE INVENTION

Figure 1:
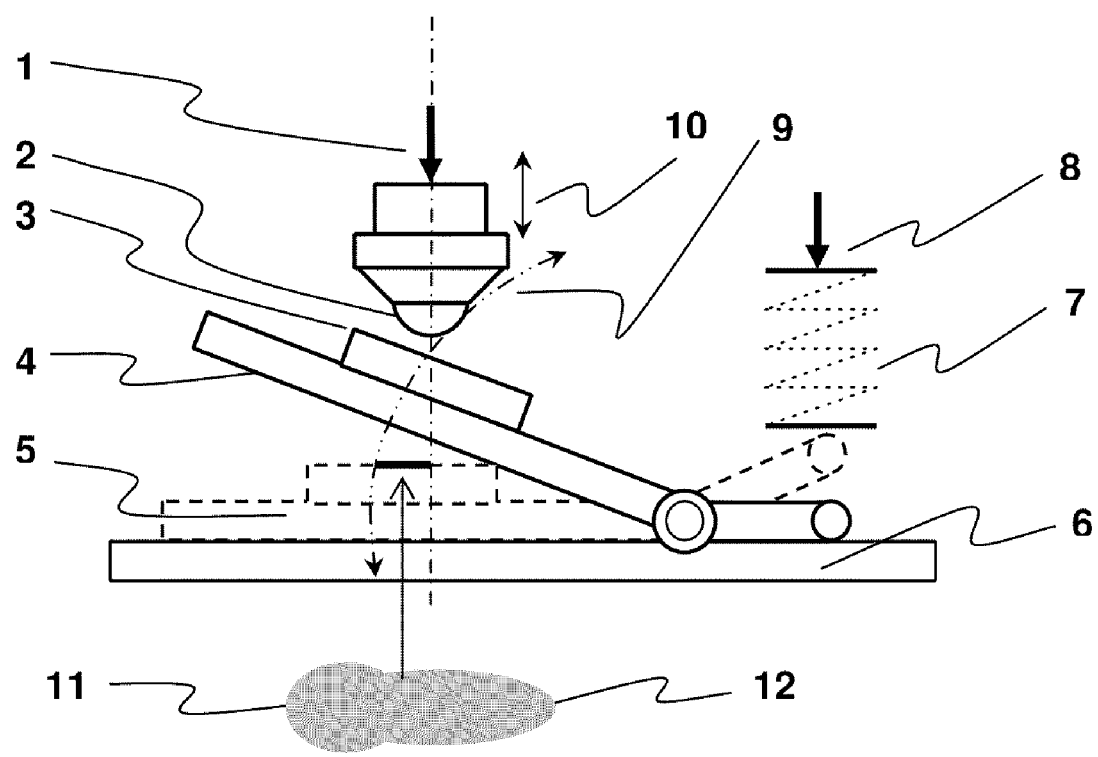
FIG. 1. Schematic drawing of the cyclic impact-sliding fatigue wear testing instrument.

This disclosure is a cyclic impact-sliding fatigue wear tester that produces cyclic impact motions and reciprocating sliding motions with high dynamic impacting and sliding contact stresses. As shown in FIG. 1, the testing instrument comprises one driving force generation device made of an air cylinder, electromagnetic cell or piezoelectric transducer to produce a driving force 1; one impacting body 2, made of steel, WC or ceramic balls, connected to the shaft of the driving force generation device; one rocker 4 used as the sample 3 holder on one one arm; one spring 7 as a rebounding force generation device used to apply the pre-loading force 8 on the other arm of the rocker; one rigid frame 6 to hold all the above parts together; one driving force control system; one switch control system; one load cell; and one data acquisition system to measure the impact force during the impacting and the pressing force during the sliding. The impacting ball 2 moves up and down 10 regulated by the driving device and switch control system, and one arm of the rocker is consequently swung 9 to the position 5. Then the arm goes back to its original position due to recoil of the compressed spring on the other arm of the rocker. For each testing cycle, the ball first impacts and then slides on the tested sample surface. The wear scar includes an impact crater 11 head and a sliding track 12 tail. The gap between the impact ball and sample surface is called a distance d. A large gap will have a large impact force at a given drive force. The normal load during the sliding is set by and is equal to the driving force.

During the impact-sliding fatigue wear test, a hard ball (the impact body) is set in a vertical oscillating motion with a driving force $F_d$. The impact force, F, is determined by the driving force, $F_d$, impact mass, m, impact ball to sample distance, d.

$$d = \frac{1}{2}at^2 = \frac{1}{2}\frac{F_d + mg}{m}t^2 \quad (1)$$

a is the acceleration rate and t is the traveling time of the ball before hitting the sample surface. The velocity of impact mass reaching the sample surface is given by $$v = at = \frac{F_d + mg}{m}t = \sqrt{2d\frac{F_d + mg}{m}} \quad (2)$$

The impact kinetic energy E is given by $$E = \frac{1}{2}mv^2 = d(F_d + mg) \quad (3)$$

Therefore, the impact energy and thus impact force can be controlled by adjusting the driving force and the gap distance. The normal force on the tested sample during the sliding motion of the test is equal to the driving force. The selection of the driving force is based on the pressing force requirement for simulation of contact stress conditions in real applications subjected to sliding wear problems. The gap distance is varied for the provision of different impact energies and forces.

The resulting impact force is actually assessed by means of a load cell. The test response is the critical number of loading cycles until the sample surface shows obvious failures. The impact and reciprocating sliding frequency is set up in a range of 1 to 20 Hz. The number of cycles is set up preferably at 1,000 to 100,000 cycles. The tester produces the loads with 0.5-4.5 GPa maximum contact pressure during the tests to simulate actual stresses applied to, for instance, dies and coatings in metal-forming production. After a selected number of testing cycles, the wear conditions and failure behaviors on sample surfaces and cross sections are investigated using optical microscopy and scanning electron microscopy.

Figure 2:
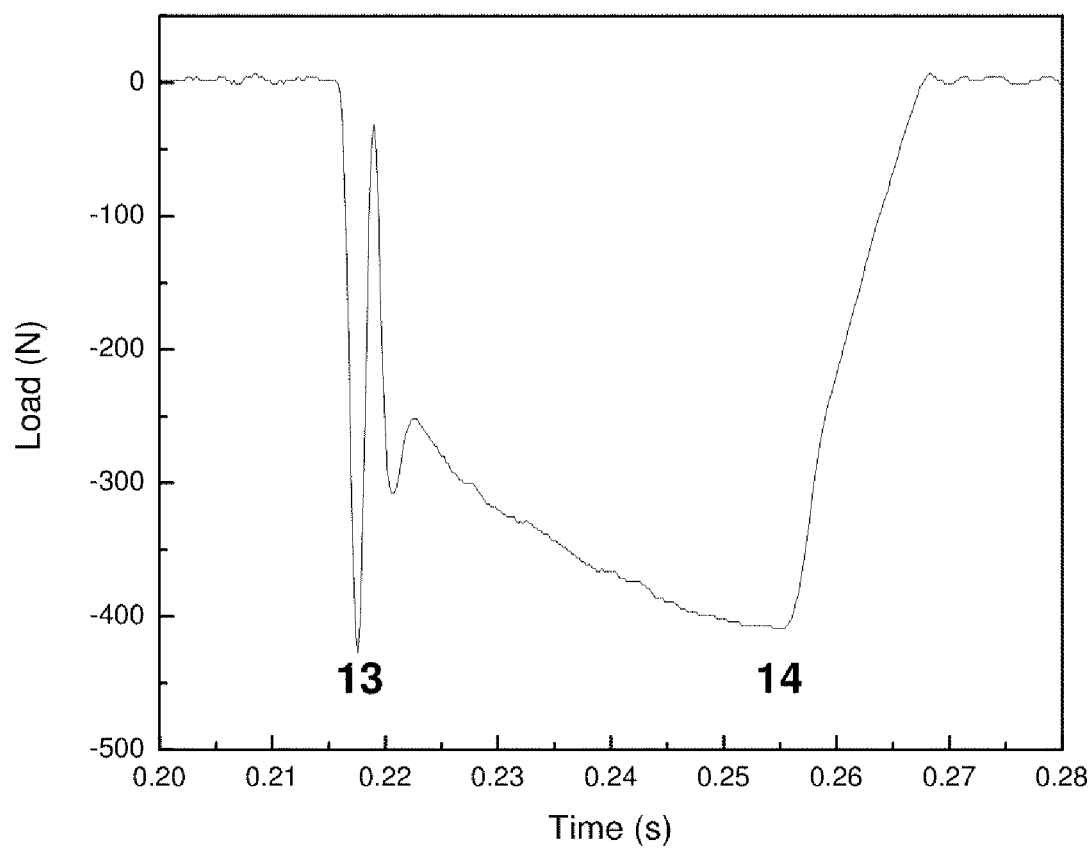
FIG. 2. A typical impact and pressing force curve of each cycle during the test.

The invented testing instrument is used to reveal five failure mechanisms of a coating and substrate:

Adhesive failures, that is, peeling
Cohesive failures, that is, chipping
Fatigue cracks
Substrate plastic deformation
Material transfer from the counterface impacting body A typical load curve includes two parts, an impact force 13 and a buildup force 14, in each cycle, as shown in FIG. 2. The amplitude of the impact load is controlled by adjusting the distance d from the impact ball to the tested sample surface without changing other conditions. The amplitude of the impact load is also controlled by adjusting the driving force without changing the distance d. After the short impacting period, a static load is built up and is finally equal to the driving force. When the distance d is set up to be zero, the impulse disappears and the driving force only works at continuous contact mode. For the case of an air cylinder that provides the driving force, the change of air pressure in the air cylinder will produce the required normal force for the sliding wear test.

Figure 3:
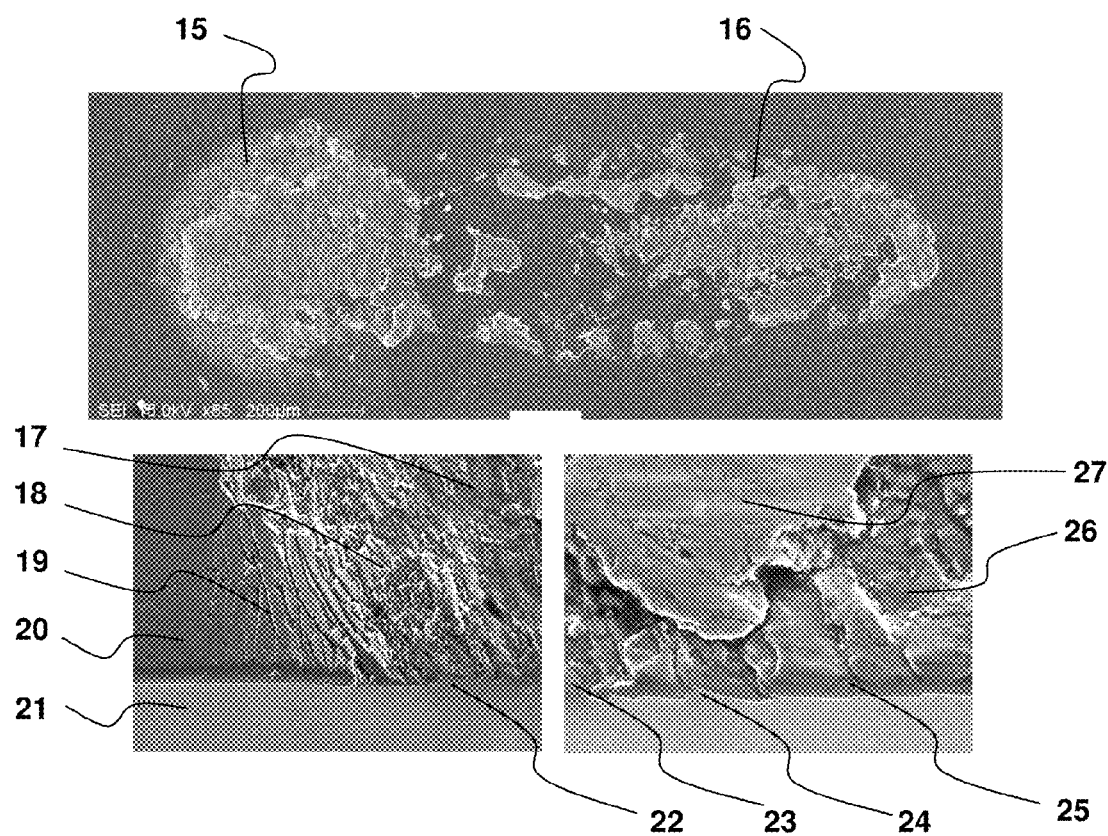
FIG. 3. Scanning electron microscope images of an impact-sliding fatigue wear scar with typical failure behaviors of peeling, chipping, fatigue cracking and material transferring.

An impact-sliding fatigue wear scar consists of an impact crater 15 and a sliding track 16 as shown in FIG. 3. The peeling 17 and 23, chipping 18 and 26, fatigue cracking 19 and 25, substrate plastic deformation 22 and 24, and the material transferring 27 from the impacting body are the failure mechanisms of a coating 20 and substrate 21, FIG. 3.

The present invention is further described with reference to the following examples Example 1

A load curve includes two parts, an impact force 13 and a build-up pressing force 14, in each cycle, as shown in FIG. 2. The impact force is adjusted to be in a range of 0 to 3000 Newtons (N). The pressing force is adjusted to be in a range of 10 N to 1500 N. When the gap between the impact ball and the tested sample is 0, the impact force is 0 N, which means that the test is operating only in the sliding mode. Different combinations of an impact force and a pressing force are obtained by varying the gap distance d and the driving force $F_d$ provided by the driving device. For the case that the driving device is an air cylinder, different driving forces are obtained by regulating its air pressure. FIG. 2 is an example of a load curve of one cycle where the combination of a 400 N impact force and a 400 N pressing force at a frequency of 10 Hz is presented. After a short period of impacting under a 400 N load, a quasi-static pressing load 400 N is built up and is finally equal to the driving force 400 N. Air pressure in the air cylinder will produce the required normal force for the sliding wear test.

Example 2

The sample 3 holder on the rocker 4 in FIG. 1 is added with a heating element. For instance, a heating tube is embedded into the sample holder and rocker so that the tested sample can be heated up to 600° C. Thus, temperature and annealing effects can be studied.

Example 3

An ultrasonic sensor and piezoelectric transducer are added onto the sample 3 holder and the shaft of the driving device 1. The sensor and transducer are used to detect the signals of the sample failure. When the peeling, chipping and fatigue cracking occur, ultrasonic sounds will be generated. By capturing the ultrasonic signals, the number of the testing cycles before failure can be determined.

Example 4

A force sensor is added onto the sample 3 holder. The sensor is used to measure friction forces during the sliding motion. When the peeling, chipping, fatigue cracking and material transferring occur, friction forces will suddenly be changed. By capturing the significant change of friction forces, the number of the testing cycles before failure can be determined.

Example 5

A digital camera microscope is added and fixed onto the instrument frame 6. The microscope is used to take snapshots and monitor the severity of the sample 3 failures at the locations of the impact crater 11 and sliding wear scar 12.

Example 6

The sample 3 to be tested is a hard coating material deposited on a substrate. The hard coating is prepared by physical vapor deposition (PVD), chemical vapor deposition (CVD), electroplating, electroless plating, thermal spraying or plasma spraying. The substrate is a heat-treated titanium alloy, cast iron, or steel material including H13, P20, S7, M2, and D2.

Example 7

The sample 3 to be tested is a heat-treated steel. The heat treatment includes carburizing, nitriding, nitrocarburizing, laser hardening, flame hardening or induction hardening.

Example 8

The sample 3 to be tested is a nitride, carbide, or oxide ceramic material. The nitride material includes $Si_3N_4$, AlN, BN, TiN, and CrN. The carbide material includes SiC, CrC and TiC. The oxide material includes $Al_2O_3$, $TiO_2$, $SiO_2$, MgO and $ZrO_2$.

Example 9

The sample 3 to be tested is a tungsten carbide (WC) material. The WC cement used for the tooling industry can have a colbert (Co) content of 5 wt %-40 wt %.

Example 10

The impact-sliding fatigue wear test can be conducted in both dry and lubricant conditions. The lubricant reduces the severity of the failure and increases the number of test cycles before the tested sample fails. The phenomena are used to study lubricating effects of different lubricants.

Example 11

The impact-sliding fatigue wear test is conducted in various testing conditions, including a high number of impacts, high impact frequency and high sliding speeds, to study the effects of impact cycles and heat generated during the test.

Example 12

During the impact-sliding fatigue wear test, the impact body 2 material is a metallic material, including steel, cast iron, Ni alloy, Cu alloy, aluminum alloy, titanium alloy, and magnesium alloy. The counterface material transferring appears after the test.

Example 13

In the impact-sliding fatigue wear test, the impact body 2 material is a ceramic material including WC and $Al_2O_3$. Due to their high hardness and elastic modulus, the ceramic material usually causes more damage to the tested sample than a metallic impact ball material.

Example 14

Before the impact-sliding fatigue wear test, the gap distance d between the impact ball 2 and the tested sample surface 3 is set up to be zero, thus, the impact force is zero. This setup provides a pure sliding wear test without an impact motion. The sliding movement performs at varied inclined angles during each reciprocating cycle due to the rocker 4 swung 9 under the up and down motions 10 of the ball 2.

Example 15

The test instrument is set up with different initial impacting angles by adjusting the rotation position of the rocker 4 in FIG. 1. Thus, different shear forces are introduced into the tested sample surface 3. The severity of sample failure varies with the magnitudes of the forces.

Example 16

Before the impact-sliding fatigue wear test, the rocker 4 is fixed at the position 5, which provides a pure impact test without a sliding motion.

Example 17

Before the impact-sliding fatigue wear test, the rocker 4 is fixed at a selected angle between the highest position 4 and the lowest position 5, which provides an inclined impact test without a sliding motion.

Example 18

The sample 3 holder is added with a container with sand. The sand is used to study erosion and abrasion wear under the impact and sliding motions.

Example 19

The sample 3 holder is added with a container with liquid. The liquid as a corrosion media is used to study corrosion effects under the impact and sliding contact stresses.

Example 20

For the impact-sliding fatigue wear test, the impact and reciprocating sliding frequency is set up in a range of 1 to 20 Hz. The number of cycles is set up preferably at 1,000 to 100,000 cycles. The tester produces loads of 0.5-4.5 GPa maximum contact pressure during the tests to simulate actual stresses applied to, for instance, dies and coatings in production metal forming. After a selected number of testing cycles, the wear conditions and failure behaviors on sample surfaces and cross-sections are investigated using optical microscopy and scanning electron microscopy.

The invented testing instrument typically reveals five failure mechanisms of a coating and substrate: (i) adhesive peeling failures, (ii) cohesive chipping failures, (iii) fatigue cracking, (iv) plastic deformation of substrate and (v) material transfer from the counterface impacting body.

What is claimed is:

1. A testing instrument for investigation into failure behavior of a sample subject to impact and sliding forces, the said instrument comprising:
   a driving force generation device,
   an impact body connected to the driving device,
   a rocker with two arms,
   a sample holder on one arm of the rocker,
   a rebounding force generation device pushing against the other arm of the rocker,
   a frame to hold the driving device, the rocker and the rebounding device together,
   a driving force control system,
   a switch control system for the driving device,
   a load cell for driving and rebounding force measurement, and
   a data acquisition system for the load cell.

2. A testing instrument according to claim 1, which produces an impact motion and a reciprocating sliding motion.

3. A testing instrument according to claim 1, wherein the driving force generation device produces an impact force on a sample surface to be tested during the impact motion and magnitude of the impact force is adjusted by changing the distance between the impact body and the sample surface.

4. A testing instrument according to claim 1, wherein the driving force generation device produces a pressing force on a sample surface to be tested during the sliding motion and magnitude of the pressing force is equal to the driving force.

5. A testing instrument according to claim 1, which is set up with different impacting angles by adjusting initial rotation position of the rocker.

6. A testing instrument according to any one of claims 1 and 2, wherein the rocker holds a sample to be tested and swings when the impact body first impacts and then slides on the sample surface in each test cycle.

7. A testing instrument according to any one of claims 1 and 2, which produces the impact and sliding motions of each cycle in the range of 1 to 20 Hertz in frequency, which is controlled by the switch control system of the driving device.

8. A testing instrument according to any one of claims 1 and 2, which performs the impact and sliding motions for 1,000 to 100,000 cycles under a load in the range of 0.5-4.5 GigaPascals of maximum contact pressure, determined by the load cell and the data acquisition system.

9. A testing instrument according to claim 1, wherein the driving force generation device is made of an air cylinder, an electromagnetic cell or a piezoelectric transducer.

10. A testing instrument according to claim 1, wherein the impact body is a ball made of metallic, tungsten carbide or ceramic.

11. A testing instrument according to any one of claims 1 and 3, wherein the sample to be tested is a hard coating, hardened steel, tool steel, titanium alloy, tungsten carbide or ceramic material.

12. A testing instrument according to claim 1, which is used to investigate failure behavior, including peeling, chipping, fatigue cracking, substrate plastic deformation, and material transferring, of biomedical implants, components, tools and coatings.

13. A testing instrument according to claim 1, wherein the sample holder is able to have a load cell to measure friction forces during the test.

14. A testing instrument according to claim 1, wherein the sample holder is able to have an ultrasonic sensor for monitoring failure signals.

15. A testing instrument according to claim 1, which is added with a digital camera microscope for taking images of the impact and sliding wear scars and for monitoring severity of sample failures.

16. A testing instrument according to claim 1, wherein the sample holder is able to have a container of sands and liquids for study on erosion, abrasion and corrosion effects.

17. A testing instrument according to claim 1, wherein the sample holder is added with a heating stage for investigation of temperature effects.

* * * * *